(12) United States Patent
Campbell et al.

(10) Patent No.: US 8,543,221 B2
(45) Date of Patent: Sep. 24, 2013

(54) EXTERNAL SYSTEMS FOR DETECTING IMPLANTABLE NEUROSTIMULATION LEADS AND DEVICES, AND METHODS OF USING SAME

(75) Inventors: Michael J. Campbell, Sachse, TX (US); William L. Winstrom, Austin, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 13/596,592

(22) Filed: Aug. 28, 2012

(65) Prior Publication Data
US 2013/0079848 A1 Mar. 28, 2013

Related U.S. Application Data

(60) Provisional application No. 61/538,018, filed on Sep. 22, 2011.

(51) Int. Cl.
*A61N 1/08* (2006.01)
(52) U.S. Cl.
USPC .............................. 607/115; 607/60
(58) Field of Classification Search
None
See application file for complete search history.

(56) References Cited

U.S. PATENT DOCUMENTS

| 2004/0167587 A1* | 8/2004 | Thompson | 607/60 |
| 2007/0088405 A1* | 4/2007 | Jacobson | 607/59 |
| 2011/0202112 A1* | 8/2011 | Ruais | 607/60 |

OTHER PUBLICATIONS

David Abejon, MD et al.; "Peripheral Nerve Stimulation or Is It Peripheral Subcutaneous Field Stimulation; What is in a Moniker?"; Jan. 13, 2009; Http://onlinelibrary.wiley.com/doi/10.1111/j.1525-1403.2009.00192.x/full ; 4 pgs.
"Precision Instrumentation Amplifier AD624"; Analog Devices, Inc.; Rev. C; 16 pages; 1999.
The British Pain Society's "Spinal Cord Stimulation for the Management of Pain: Recommendations for Best Clinical Practice", ©The British Pain Society 2009, ISBN: 0-9546703-7-X; pp. 1-56.
Tracy Cameron, Ph.D; Safety and Efficacy of Spinal Cord Stimulation for the Treatment of Chronic Pain; a 20-year Literature Review; J. Neurosurg (Spine 30) 100:254-267, 2004.
Chen et al.; "ECG Measurement System"; ECG Measurement System; http://www.cisl.columbia.edu/kinget_group/student_projects/ECG%20Report/E6001%20E..; 9 pages; Aug. 2, 2010.

(Continued)

*Primary Examiner* — Carl H Layno
*Assistant Examiner* — Paula J Stice

(57) ABSTRACT

Embodiments herein include an external system and method to detect an implanted lead coupled to an implanted neurostimulation device (INSD). The system and method comprise a handheld probe having electrodes configured to be positioned external to a surface of a patient and proximate to a region of the patient having the implanted lead for an implanted INSD. The electrodes are configured to measure a stimulation output from the implanted lead of the INSD. The system and method include a controller coupled to the electrodes to receive measured signals from the electrodes. The measured signals represent the stimulation output of the INSD. The controller processes the measured signals to obtain lead information. The system includes a user interface to present the lead information to a user. The lead information is indicative of at least one of an operation of the lead and a position of the lead.

6 Claims, 10 Drawing Sheets

(56) References Cited

OTHER PUBLICATIONS

Samer N. Narouze, MD et al.; "Supraorbital Nerve Electric Stimulation for the Treatment of Intractable Chronic Cluster Headache: A Case Report"; pain Management Department, The Cleveland clinic Foundation, Cleveland OH, USA, Apr. 30, 2007: 1100-1102.

Richard M. Paicius, MD et al.; "Peripheral Nerve Field Stimulation in Chronic Abdominal Pain"; Pain Physician; 2006; 9:261-266, ISSN 1533-3159.

"Applications for Pico Products—Electrocardiogram (ECG) Project for DrDaq"; Electrocardiagram (ECG/EKG) project for the DrDAQ data logger; http://www.picotech.com/applications/ecg.html; 8 pages; Aug. 2, 2010.

KL Reed et al.; "Combined Occipital and Supraorbital Neurostimulation for the Treatment of Chronic Migraine Headaches: Initial Experience"; Cephalalgia, International Headache Society; CEP.sagepub. com; Published online Feb. 15, 2010; 30(3) 260-271.

* cited by examiner

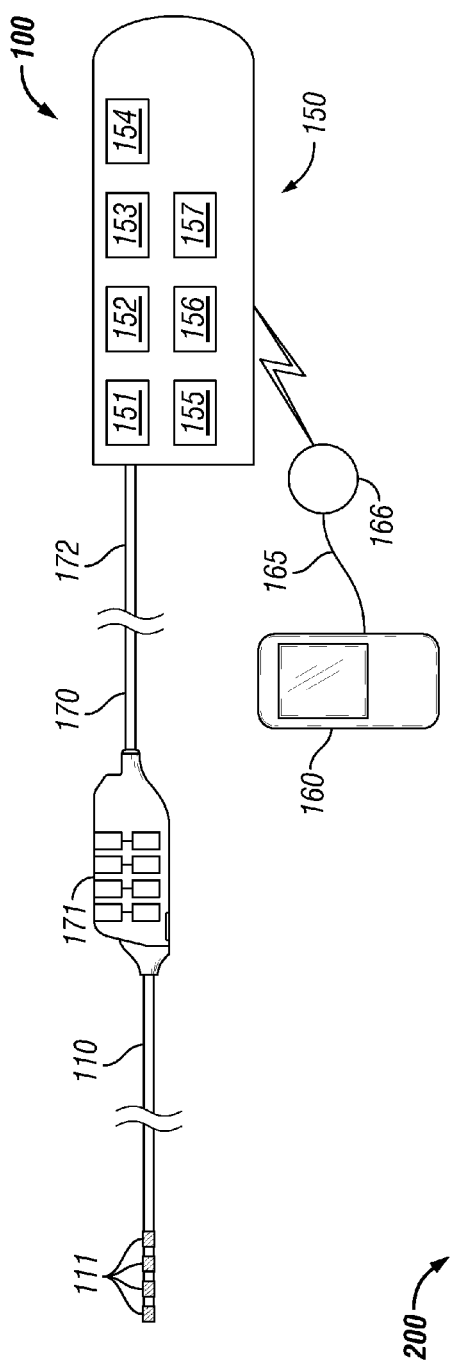
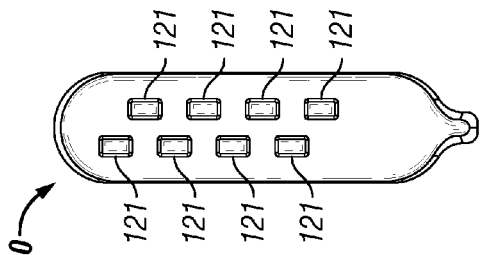
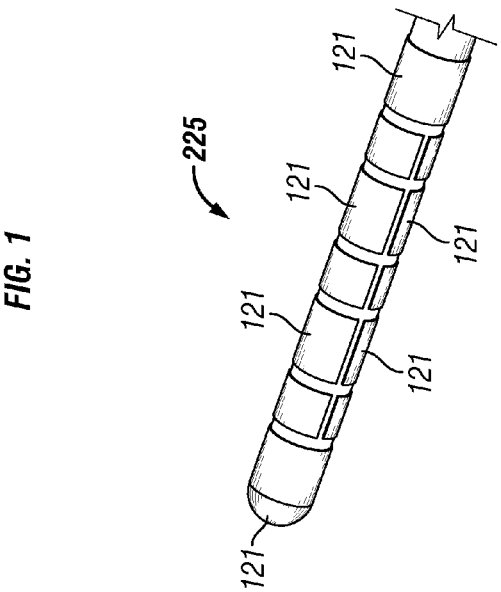
FIG. 1
FIG. 2A
FIG. 2B
FIG. 2C

EXTERNAL SYSTEMS FOR DETECTING IMPLANTABLE NEUROSTIMULATION LEADS AND DEVICES, AND METHODS OF USING SAME

CROSS-REFERENCE TO RELATED APPLICATIONS

This application claims the benefit of U.S. Provisional Application No. 61/538,018, filed Sep. 22, 2011, which is incorporated herein by reference.

BACKGROUND OF THE INVENTION

Embodiments of the present invention generally relate to neurostimulation systems, and more particularly to methods and systems to monitor an implanted lead and implanted neurostimulation device.

Neurostimulation (NS) systems are systems that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

An NS system generally includes a NS device (NSD) that includes a pulse generator, with the NSD coupled to one or more stimulation leads. A stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors that are adapted to receive electrical pulses. The distal end of a respective stimulation lead is implanted within a desired area, such as the epidural space, to deliver the electrical pulses to the appropriate nerve tissue, such as within the spinal cord that corresponds to the dermatome(s) in which the patient experiences chronic pain. The stimulation leads are then tunneled to another location within the patient's body to be electrically connected with a pulse generator or, alternatively, to an "extension."

The NS device is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

The NS device is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

After implantation, it may become desirable to monitor various parametric properties of the NS system. For example, it may be desirable to analyze the operation of the NS device, such as the discharge mode, pulse sequency, pulse width and frequency for the stimulation output of the NS device. Further, it may become desirable to locate the NS lead and more specifically, to locate the position and/or identity inoperative and operative electrodes on the NS lead. After implementation, the potential exists for NS leads to move or migrate within the patient. Heretofore, there has been no reliable and practical mechanism to readily identify lead migration. Also, there is no reliable and practical method for a physician or representative to locate the lead's position in connection with reprogramming or physical intervention. Today, physicians use fluoroscopy systems to locate a lead that has moved within the patient. Once the new position of the lead is identified, the physician then reprograms the lead, such as to use a different set of electrodes on the lead to deliver the stimulus output. This method exposes the patient to radiation each time a fluoroscopy is performed, which is not desirable.

Also, presently there is no reliable and practical way to identify lead malfunctions. Lead malfunctions may occur due to physical failure or breaks within the lead conduction and/or electrical failures within the NS device. Today when a physical failure or break causes a lead to operate intermittently or not at all, the intermittent and open leads are not easily diagnosable down to the electrode.

Further, today no tool exists that enables data logging for research to enable patient anomalies to be recorded in connection with stimulation outputs while an NS lead is in the patient. Also, today problems occur in the emergency medical field because an unconscious person cannot inform an EMT that the person has an implantable device, and cannot inform the EMT of the location of the implantable device. Hospitals using MRI's and X-ray machines may not have a quick method of determining what type of device the patient has within them, nor the location of the device.

A need remains for systems and methods that detect an implanted lead and/or an implanted neurostimulation device and that provide parametric information in connection therewith.

SUMMARY

Embodiments of the present invention include an external detector with a probe that has an instrumentation amplifier coupled to two or more closely spaced surface electrodes. The probe surface electrodes search for implanted electrodes of an NS lead by externally contacting the skin of the patient at different distances from the electrical source and obtaining measurements that are used to locate the NS lead active electrodes or electrical field output source. The external device accurately amplifies actual stimulation and displays information, such as graphs, oscilloscope images and the like, that are indicative of stimulation output from the implanted electrodes. For example, the display may present a graph corresponding to the electrical occurrence, where the amplitude of the graph corresponds to the stimulation output. The amplitude of the measured signal increases as the probe moves closer to the implanted electrodes that are generating the stimulation output because the electrical field grows stronger when the external probe electrodes are moved closer to the stimulation source.

Embodiments herein include an external system to detect an implanted lead coupled to an implanted neurostimulation device (INSD). The system comprises a handheld probe having electrodes configured to be positioned external to a surface of a patient and proximate to a region of the patient having the implanted lead for an implanted INSD. The electrodes are configured to measure a stimulation output from the implanted lead of the INSD. The system includes a controller coupled to the electrodes to receive measured signals from the electrodes. The measured signals represent the stimulation output of the INSD. The controller processes the measured signals to obtain lead information. The system includes a user interface to present the lead information to a user. The lead information is indicative of at least one of an operation of the lead and a position of the ISND lead.

Optionally, the lead information may include at least one of discharge mode, pulse width and frequency for the stimulation output of the INSD; a presence, signal strength, duration and shape for the stimulation output of the INSD; electrical occurrence of, and electrical anomalies in, the stimulation output of the INSD; i) information to locate the lead in the patient and ii) information to identify improper operation of the lead.

Optionally, the external surface electrodes include first and second electrode inputs closely spaced proximate to one another to be moved along skin of the patient while locating the lead. An amplifier compares the measured signals to obtain a difference signal, the difference signal increasing as the electrodes move closer to a source of the stimulation output.

In other embodiments, a method is provided to detect an implanted lead of an implanted neurostimulation device (INSD). The method comprises positioning a handheld probe having electrodes external to a surface of a patient and proximate to a region of the patient having the implanted lead for an implanted INSD and configuring the electrodes to measure a stimulation output from the implanted lead of the INSD. The method further comprises receiving measured signals from the electrodes, where the measured signals are representative of the stimulation output of the INSD; and processing the measured signals to obtain INSD lead information. The method then presents the lead information to a user, where the lead information is indicative of at least one of an operation of the lead and a position of the ISND lead.

Optionally, the presenting operation includes displaying to the user a graphical representation of the measured stimulation output including a pulse sequence having at least one pulse void therein corresponding to a location in the pulse sequence associated with a failed electrode. Optionally, the presenting operation includes displaying to the user a graphical representation of a measured pulse sequence that includes a blank area in the pulse sequence where a pulse should have been measured, but did not occur due to a faulty electrode. Optionally, the presenting operation includes co-displaying measured and programmed stimulation outputs for comparison by the user to determine where a fault exists.

BRIEF DESCRIPTION OF THE DRAWINGS

FIG. 1 depicts a neurostimulation system according to some representative embodiments.

FIGS. 2A-2C respectively depicts stimulation portions for inclusion at the distal end of a lead according to some representative embodiments.

DETAILED DESCRIPTION

Figure 3:
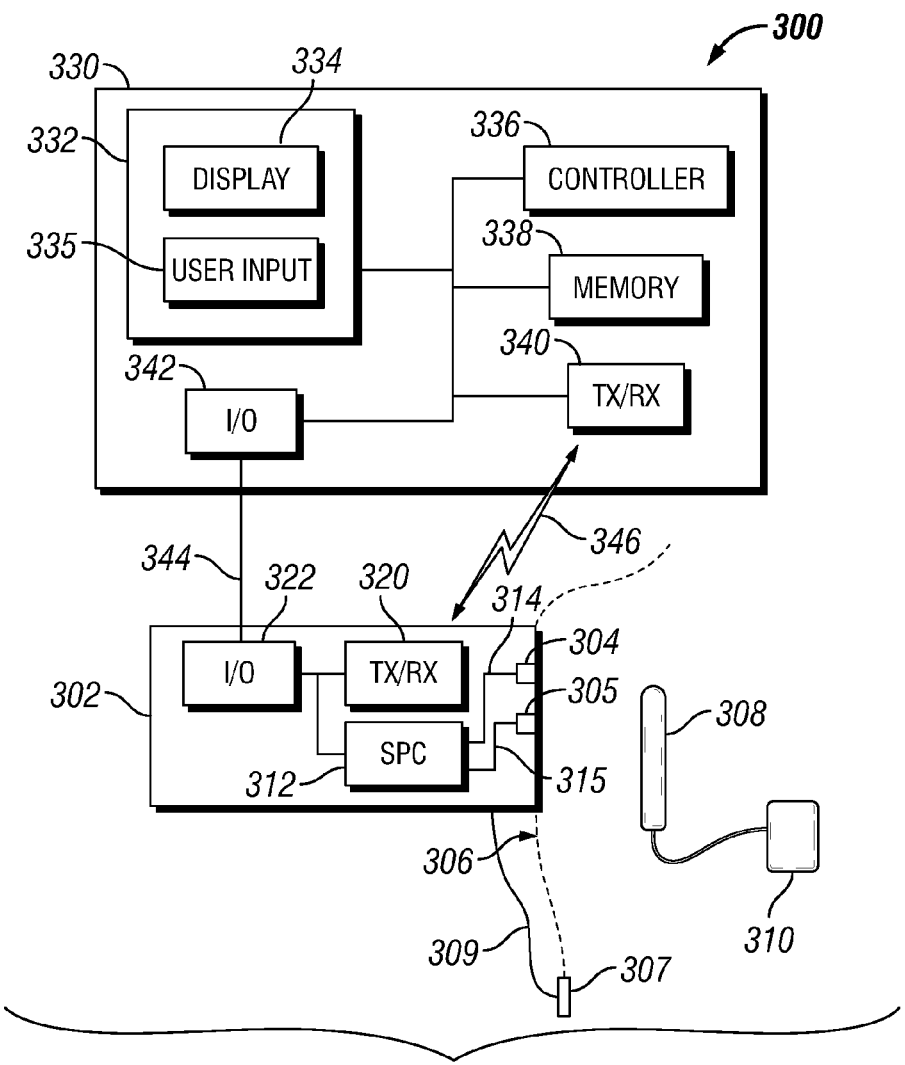
FIG. 3 illustrates a system for detecting NS devices and NS leads in accordance with an embodiment.

Embodiments herein provide a non-intrusive tool to display electrical occurrence, diagnose electrical anomalies, and/or locate active leads in the patient while an NS device is operating in the patient. Also the external detector affords the emergency medical field a quick response small hand held tool to diagnose malfunctioning electrical medical devices. Embodiments described here can be implemented in various ways, such as a handheld wireless device utilizing a pickup coil and circuitry to amplify and digitize the measured signal into readable measurements such as discharge mode, pulse width, and frequency. As another exemplary implementation, the external detector can be performed in a contactless manner. The detector may display the presence of the measured signals and/or quantify signal strength, duration, shape and other related parametric properties, thereby enabling non-intrusive diagnosis of the medical device operation, performance and strength thus giving operational confirmation.

Embodiments herein provide a handheld stimulation analysis and lead locator device. Other applications may include a computer interface which affords real time analysis and physician program tuning. The analysis and/or tuning may utilize computer models that provide data for creating or tuning more efficient electrical fields for the NS device, thereby enabling more precise programming for pain management personalized to the individual patient. Embodiments herein provide a user friendly tool for physicians and a tool that may facilitate studies. These tools and the studies based thereon may enable new products to become more efficient and easier to use. These tools and the studies based thereon may enable programmable devices to be more readily available on the market.

FIG. 1 depicts a neurostimulation (NS) system 100 that generates electrical pulses for application to tissue of a patient according to one embodiment. For example, NS system 100 may be adapted to stimulate spinal cord tissue, peripheral nerve tissue, deep brain tissue, cortical tissue, cardiac tissue, digestive tissue, pelvic floor tissue, or any other suitable tissue within a patient's body.

NS system 100 includes an implantable NS device 150 that is adapted to generate electrical pulses for application to tissue of a patient. The implantable NS device 150 typically comprises a metallic housing that encloses controller 151, pulse generating circuitry 152, charging coil 153, battery 154, far-field and/or near field communication circuitry 155, battery charging circuitry 156, switching circuitry 157, etc. of the device. Controller 151 typically includes a microcontroller or other suitable processor for controlling the various other components of the device. Software code is typically stored in memory of the NS device 150 for execution by the microcontroller or processor to control the various components of the device.

The NS device 150 may comprise a separate or an attached extension component 170. If extension component 170 is a separate component, extension component 170 may connect with the "header" portion of NS device 150 as is known in the art. If extension component 170 is integrated with NS device 150, internal electrical connections may be made through respective conductive components. Within NS device 150, electrical pulses are generated by pulse generating circuitry 152 and are provided to switching circuitry 157. The switching circuit connects to outputs of NS device 150. Electrical connectors (e.g., "Bal-Seal" connectors) within connector portion 171 of extension component 170 or within the IPG header may be employed to conduct the stimulation pulses. The terminals of one or more stimulation leads 110 are inserted within connector portion 171 or within the header for electrical connection with respective connectors. Thereby, the pulses originating from NS device 150 are provided to stimulation lead 110. The pulses are then conducted through the conductors of lead 110 and applied to tissue of a patient via electrodes 111. Any suitable known or later developed design may be employed for connector portion 171.

For implementation of the components within NS device 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within NS device 150. Different pulses on different electrodes may be generated using a single set of pulse generating circuitry using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO/2001/093953 A1, entitled "NEUROMODULATION THERAPY SYSTEM," which are incorporated herein by reference. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Neurostimulation lead(s) 110 may comprise a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

FIGS. 2A-2C respectively depict stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Patent Publication No. 20110072657, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Although not required for all embodiments, the lead bodies of lead(s) 110 and extension component 170 may be fabricated to flex and elongate in response to patient movements upon implantation within the patient. By fabricating lead bodies according to some embodiments, a lead body or a portion thereof is capable of elastic elongation under relatively low stretching forces. Also, after removal of the stretching force, the lead body is capable of resuming its original length and profile. For example, the lead body may stretch 10%, 20%, 25%, 35%, or even up or above to 50% at forces of about 0.5, 1.0, and/or 2.0 pounds of stretching force.

The ability to elongate at relatively low forces may present one or more advantages for implantation in a patient. For example, as a patient changes posture (e.g., "bends" the patient's back), the distance from the implanted pulse generator to the stimulation target location changes. The lead body may elongate in response to such changes in posture without damaging the conductors of the lead body or disconnecting from pulse generator. Also, deep brain stimulation implants, cortical stimulation implants, and occipital subcutaneous stimulation implants usually involve tunneling of the lead body through tissue of the patient's neck to a location below the clavicle. Movement of the patient's neck subjects a stimulation lead to significant flexing and twisting which may damage the conductors of the lead body. Due to the ability to elastically elongate responsive to movement of the patient's neck, certain lead bodies according to some embodiments are better adapted for such implants than some other known lead body designs. Fabrication techniques and material characteristics for "body compliant" leads are disclosed in greater detail in U.S. Provisional Patent Application Ser. No. 60/788,518, entitled "Lead Body Manufacturing," filed Mar. 31, 2006, which is incorporated herein by reference.

Controller device 160 may be implemented to recharge battery 153 of NS device 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery 153 by charging circuitry 154. Charging circuitry 154 may also communicate status messages to controller 160 during charging operations using pulse-loading or any other suitable technique. For example, controller 160 may communicate the coupling status, charging status, charge completion status, etc.

External controller device 160 is also a device that permits the operations of NS device 150 to be controlled by user after NS device 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate NS device 150. The user interfaces may permit the user to move electrical stimulation along and/or across one or more stimulation leads using different electrode combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is incorporated herein by reference. Also, controller device 160 may permit operation of IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

FIG. 3 illustrates an external detector system 300 to detect an implanted lead and/or operation of an implanted neurostimulation device in accordance with embodiments herein. The detector system 300 locates leads and/or devices in numerous regions of the patient, such as along the spinal column, stomach, organs, muscles, inside the skull, along the brain stem and the like. The system 300 includes a detector 330 connected to a handheld probe 302 that has surface electrodes 304 configured to be positioned proximate and external to a surface of a patient. The probe 302 also includes a transceiver 320 and an input/output (I/O) port 322. The surface electrodes 304 and 305 are located, by the user, proximate to a region 306 of the patient having an implanted lead 308 for an implanted NS device 310. The probe 302 includes first and second electrodes 304 and 305 that are closely spaced proximate to one another and separated by an inter-electrode gap 352. The surface electrodes 304 and 305 measure a stimulation output from the implanted lead 308. The probe 302 includes signal processing circuitry (SPC) 312 that is connected through lines 314 and 315 to the surface electrodes 304 and 305. The SPC 312 receives and processes measured signals from the surface electrodes 304 and 305. The measured signals are representative of the stimulation output of the implanted lead 308. The measured signals may have positive or negative amplitude; high, medium or low amplitude; high, medium or low frequency and the like. The SPC 312 may include only a few simple electrical components, or may include a sophisticated signal processing board with a microprocessor and memory. The SPC 312 may include an A/D converter to digitize measured signals and a processor module to analyze the digitized measured signals.

The system 300 analyzes the measured signals received along lines 314 and 315 to obtain implanted lead information. For example, the SPC 312 may filter, amplify and digitize the measured signals received along lines 314 and 315 and obtain a difference signal there between. The difference signal is one example of implanted lead information. As explained hereafter, implanted lead information may be calculated by controller 336 of the detector 330 as well or instead of by the SPC 312.

The SPC 312 may include an amplifier (e.g., amplifier 500 in FIG. 5) that compares the measured signals to obtain a continuous difference signal as the probe 302 is moved. The difference signal increases as the surface electrodes 304, 305 are moved away from a source of the stimulation output. The difference signal decreases as the surface electrodes 304, 305 are moved closer to a source of the stimulation output. The difference signal is at a minimum when the surface electrodes 304, 305 are centered over an active implanted electrode.

Optionally, the probe 302 may include an additional grounding electrode 307 connected by line 309 to the probe 302. The grounding electrode 307 may be attached to another region of the patient (e.g., leg, arm, waist, chest), while the line 309 may be joined to the housing of the probe 302, to the signal processing circuitry 312 or otherwise to establish a reference ground.

The system 300 includes a non-implantable external detector 330 connected to the probe 302 over a physical two-way communications line 344 and/or a two-way wireless link 346. The detector 330 includes an I/O port 342. The line 344 is connected between the I/O ports 342 and 322. The detector 330 includes a transceiver 340 that communicates with the transceiver 320 over the wireless link 346. The physical line 344 may be one or more coaxial cables, USB lines, optical connections or any other type of link(s) that supports transfer of high speed, large bandwidth analog or digital signals and/or data. The wireless link 346 may be an infrared link, an optical link, an RF link, a microwave link, a cellular link or any other type of link any other type of link(s) that supports transfer of high speed, large bandwidth analog or digital signals and/or data. The system 300 may utilize various protocols to manage conveyance of the signals and data between the detector 330 and the probe 302.

The detector 330 and probe 302 may represent a handheld portable device that can be easily carried by a user such as a technician, doctor, EMT and the like. Optionally, the detector 330 may constitute a cell phone, PDA, laptop computer, tablet-type computer, desk top computer and the like. Optionally, the detector 330 and probe 302 may be combined into a common housing to form a single integrated portable handheld device.

The probe 302 may convey various types of implanted lead information to the detector 330. For example, the probe 302 may simply convey the measured signals to the detector 330. Alternatively, the probe 302 may convey, to the detector 330, a difference between the measured signals, and/or analysis data derived from the measured signals (e.g., lead fault results, lead location, electrode status).

The detector 330 also includes a controller 336 and memory 338. The memory 338 may store signals, information and data conveyed to and from the probe 302, such as the measured signals, difference signals, analysis data and the like. The memory 338 also stores software used to implement various analysis methods by the controller 336.

The detector 330 includes a user interface 332 that includes a display 334 to present the implanted lead information to a user and user input 335 to receive instructions and inputs from the user. The lead information may be indicative of at least one of an operation of the lead and the position of the lead. The lead information may include at least one of discharge mode, pulse width and frequency for stimulation output of the NS device 150. The lead information may include at least one a presence, signal strength, duration and shape for the stimulation output of the NS device 150 at select electrodes or at each electrode. The lead information may include at least one electrical occurrence of, and electrical anomalies in, the stimulation outputs of the NS device 150 at select electrodes or at each electrode. Optionally, the lead information may include information to locate the NS lead in the patient and/or information to identify improper operation of the NS lead.

The display 334 may illustrate a graph plotting the positive or negative amplitude of the difference signal along a vertical axis and time along the horizontal axis. As the probe 302 is moved along the patient's skin, the amplitude of the difference signal changes from a high level to a low level to near zero as the skin electrodes 304, 305 are moved from a distal, non-aligned position to an aligned position, proximate to the lead. When the display presents a near-zero graph, this indicates that the surface electrodes 304, 305 are generally centered over a source of the stimulation output. As the probe 302 is moved up/back or left/right, the signal displayed will increase/decrease and may reach a null value when centered over the implanted lead.

Figure 4A:
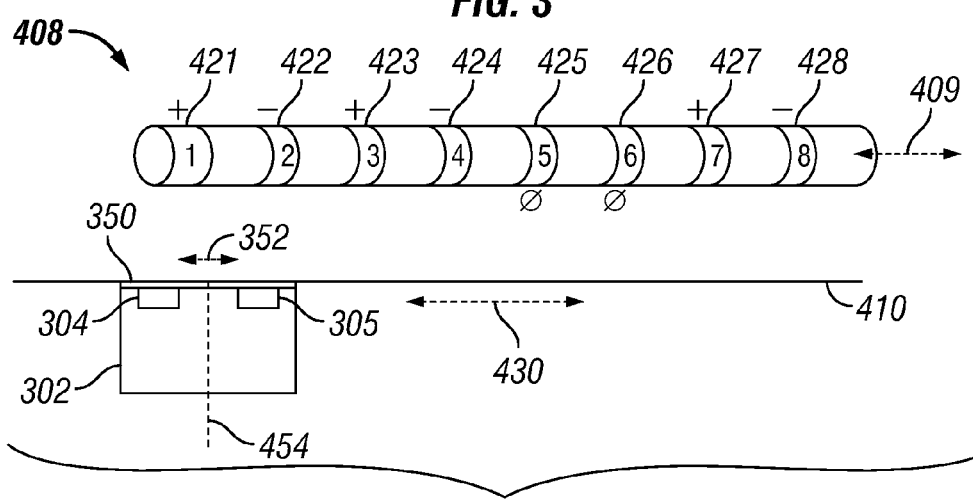
FIG. 4A illustrates an exemplary side view of a tip portion of a probe when in use to monitor or locate an NS lead in accordance with an embodiment.

FIG. 4A illustrates an exemplary side view of a tip portion of probe 302 when in use to monitor or locate an NS lead 408. As shown in FIG. 4A, an NS lead 408 is located below the skin surface 410 of a patient. The NS lead 408 includes multiple implanted electrodes 421-428 that are separately controlled by, and individually coupled to, an NS device (not shown) that may be also implanted in the patient. The implanted electrodes 421-428 may be individually controlled to deliver different types of pulses with different polarities, pulse widths, amplitudes, pulse shapes and the like. As a further example, a portion of the electrodes 421-428 may not be utilized at all and thus may deliver no stimulus pulses, such as denoted by the zeros next to the electrodes 425 and 426. Optionally, only one of electrodes 421-428 may deliver a stimulation output at one point in time, thereby permitting each electrode 421-428 to be individually analyzed. In the example of FIG. 4A, polarity signs are noted next to electrodes 421-424 and 427-428 to indicate that positive or negative pulses are output there from. It is understood that any combination of pulse shapes, pulse polarities, pulse widths and the like may be utilized, as well as numerous alternative combinations of the electrodes 421-428 in order to deliver a desired neurostimulation output and/or perform a lead analysis test by system 300.

As illustrated in FIG. 4A, the tip or distal portion of the probe 302 is located against the skin surface 410 of a patient. The surface electrodes 304-305 are located proximate or immediately adjacent to the skin surface 410 of the patient in order to facilitate sensing of electrical activity from the implanted electrodes 421-428. During operation, the probe 302 and electrodes 304-305 are moved along the skin of the patient while the NS lead outputs a programmed stimulus output. Measured signals sensed at the electrodes 304 and 305 may be compared or otherwise analyzed to obtain lead information. As the probe 302 is moved along the skin surface 410, such as in the direction denoted by the arrow 430, the measured signals at electrodes 304-305 vary and similarly cause the lead information to vary. By comparing the lead information derived from sensing at the electrodes 304 and 305, various information may be determined about the NS lead 408 such as location, operational status and the like.

Figure 5:
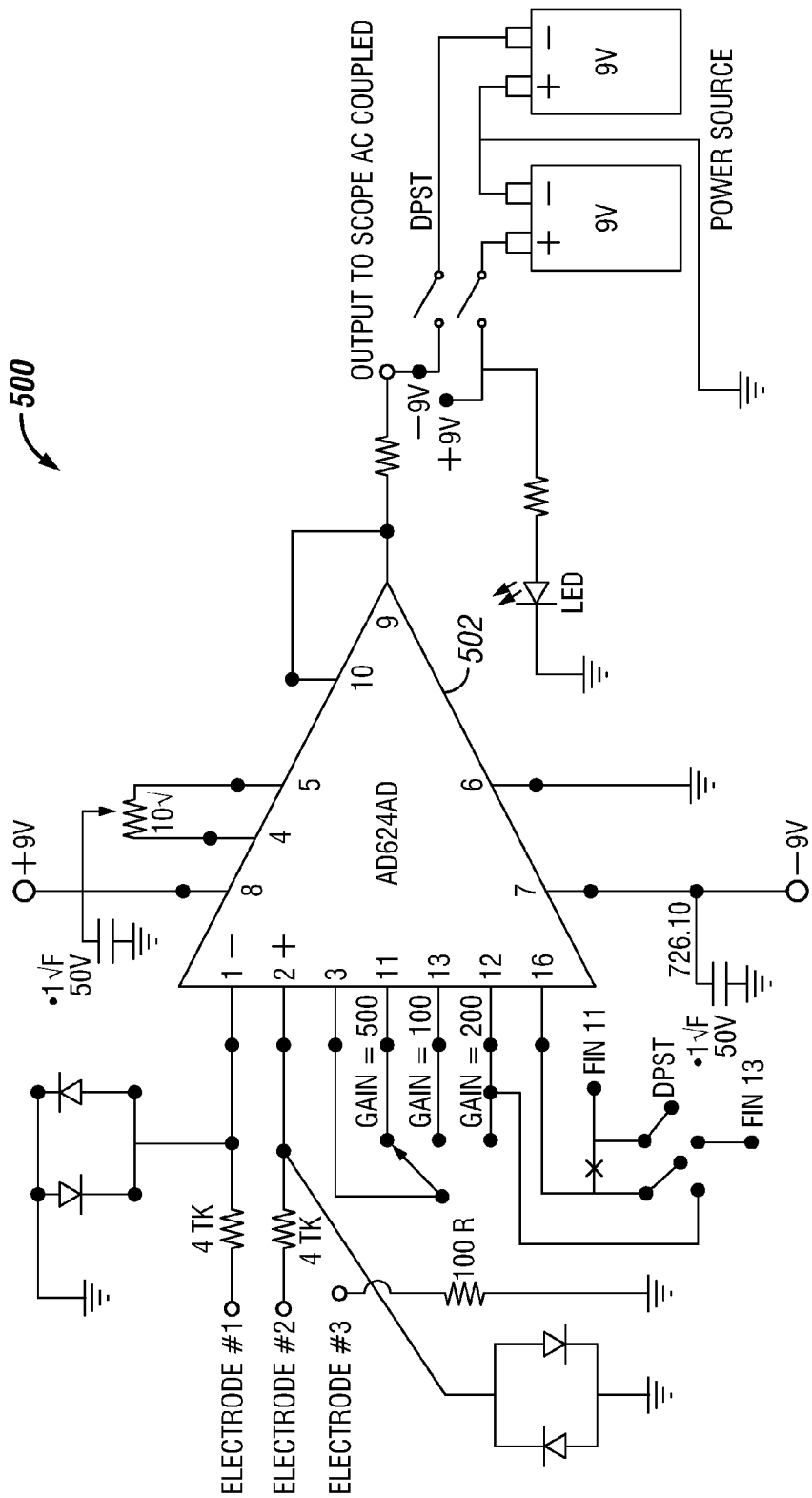
FIG. 5 illustrates a comparator circuit utilized in accordance with an embodiment.

In the example of FIG. 4A, the distal portion of the probe 302 includes a patient engaging surface 350 configured to be located against the patient skin 410. Optionally, a conductive material may be provided between the probe surface 350 and the patient skin 410 to facilitate conduction of electrical signals through the patient skin 410 to the electrodes 304-305. The electrodes 304-305 are separated by an inter-electrode gap 352 (e.g., 2 mm, 4 mm, 8 mm) about a central axis 454. The inter-electrode gap 352 may be adjusted to achieve a particular type of performance and/or achieve sensitivity to different types of electrodes. As another example, the inter-electrode gap 352 may be selected such that, when the probe is used with certain types of implanted electrodes, it avoids inversion of the source signal when measurements are taken at the strongest point in the field strength. A large inter-electrode gap 352 between electrode 304 and 305 may cause amplification of the largest difference from either the inverting or non-inverting input to the comparator 502 (FIG. 5). A smaller inter-electrode gap 352 may be desired when trying to measure field strength along a scan direction that is parallel to a source signal.

Figure 4B:
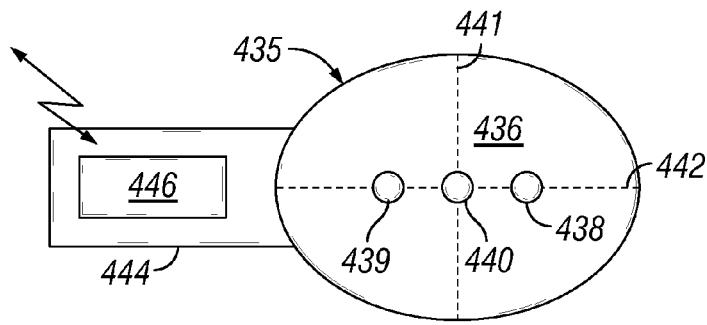
FIG. 4B-4E illustrates an exemplary side view of a tip portion of a probe when in use to monitor or locate an NS lead in accordance with an embodiment.
Figure 4C:
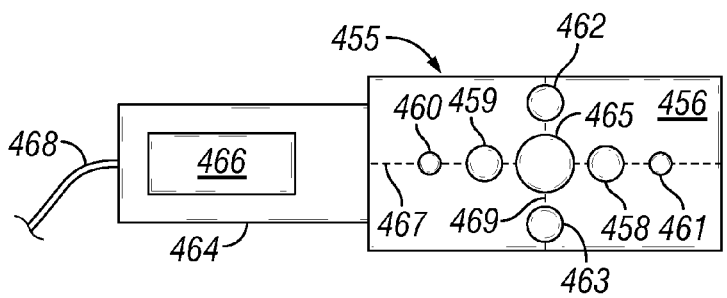
Figure 4D:
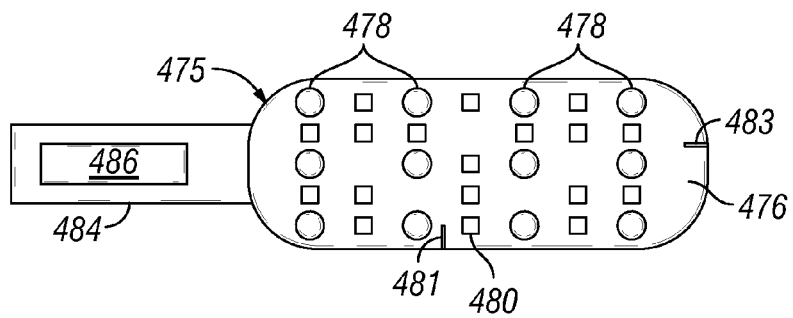

FIGS. 4B-4D illustrate bottom plan views of the probe skin contact surfaces formed in accordance with embodiments of the present invention. In FIG. 4B, a probe 435 has a skin contact surface 436 and a handle 444. The signal processing circuitry, I/O module and transceiver are located at 446 in the handle 444. The surface 436 has an electrode pair 438 and 439 located along a scan axis 442. An opening 440 may be provided through the probe 435 at a center point between the electrodes 438-439. A user may make a mark on the patient's skin, such as with a grease pin or marker through the opening 440. As another option, the opening 440 may be used during a medical procedure, such as to insert a biopsy needle or probe through the opening into the patient to manipulate or otherwise engage a desired implanted electrode or location on the lead. Longitudinal and lateral scan axes 442 and 441 may be provided as indicia on the top and bottom surfaces of the probe 435 to assist the physician in guiding movement of the probe 435 during scanning.

The electrodes may have any desired shape, such as oval, circular, semi-circular, concave, convex, triangular, square, rectangular and the like. The electrodes may each have a diameter of 2-10 mm. As another example, the electrode gap may be increased when it is desirable to provide better resolution of large signals, and closer together for better resolution of small signals. The electrode space, size and gain may be adjusted to locate different types of leads. For example, the electrodes may be spaced wider apart (e.g., inter-electrodes gap of 2-4 inches, 3 inches) to detect low amplitude stimulation outputs from electrodes deep inside the patient (e.g., 7-10 inches below the surface). Electrodes (e.g., the electronics discussed in connection with FIGS. 3 and 5) may be spaced with a medium inter-electrode gap (e.g., 2-4 cm, 2½ cm) to sense high amplitude stimulation outputs from electrodes deep inside the patient. Electrodes may be spaced near on another with a narrow inter-electrode gap (e.g., 3-6 mm, 5 mm) to sense low amplitude stimulation outputs from electrodes near the skin surface (e.g., a lead on the T5 to T9 vertebrae).

FIG. 4C illustrates a probe 455 with a skin contact surface 456 having an array of surface electrodes 458-463 distributed about an opening 465 through the probe 455. The electrodes 458-461 are aligned along a longitudinal scan axis 467 and electrodes 462-463 are aligned along a lateral scan axis 469. Electronics 466 are located in a handle 464 that has a physical cable 468 joining the probe 455 to an external detector. All or a portion of the electrodes 458-463 may be used to measure signals. For example, signals from different pairs of the electrodes 458-463 may be compared to produce multiple comparator signals. The pairs of electrodes 458-463 may be configured to be sensitive to different types of electrodes, different amplitude signals and/or different depth ranges.

The electrodes 466 may switch between subsets of the electrodes 458-463 to search for different types of signals at different depths. For example, signals from electrodes 461 and 460 may be compared initially until the probe nears a location of the lead. Signals from electrodes 458 and 459 may be compared in response to a determination that a difference signal for electrodes 460, 461 reach a certain level. Signals from electrodes 462 and 463 may be compared at the same time as signals from electrodes 458 and 459 to yield lateral and longitudinal position information, respectively.

FIG. 4D illustrates a probe 475 with a bottom skin contact surface 476 having a two dimensional array of electrodes 478 arranged in rows and columns. Electronics 486 are in the handle 484. The top surface of the probe 475 includes one or more motion indicators, such as an array of LEDs 480. The LEDs 480 are controlled by the electronics 486 based on measured signals from one or more of the electrodes. The LEDs 480 light up to provide the user with information for which direction the probe 475 should be moved to be centered over the lead. As another option, the LEDs 480 may provide information to enable the user to place a marker 481 or 483 along the edge of the probe at a center of the lead, at a distal tip of the leads, over a failed electrode on the lead and the like.

Figure 4E:
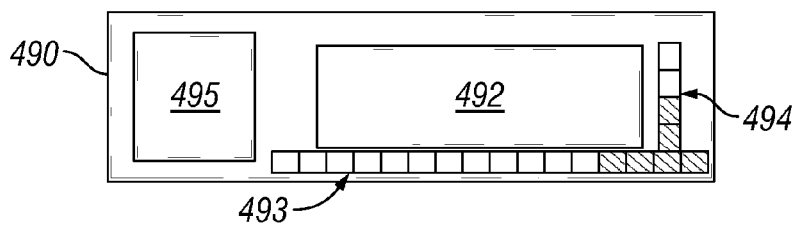

FIG. 4E illustrates a top plan view of a probe 490 formed in accordance with an embodiment. The probe 490 includes a display 492 and position adjustment output, such as LEDs 493, 494 located on the upper or top surface of the probe 490 opposite to the skin contact surface. The output (e.g., LEDs 493 and 494) turn on/off to form a series of bars to indicate where the lead is relative to a center or edge marker on the probe 490. More or few bars in the LEDs 493 and 494 light up as the probe 490 moves to a position above or aligned with the lead. A portion of the LEDs 493 and 494 are shown with cross-hatching to illustrate LEDs that are on.

The display 492 may display various additional information. For example, the display may show the type of lead identified, a graphic of the lead type, which electrode(s) has failed, lead parametric properties (e.g., pulse width, pulse shape, pulse amplitude, frequency, mode) and the like. The display 490 may present everything discussed herein in connection with any other display in the system. AS one example, the display 492 may illustrate images resembling the one or more of the images shown in FIGS. 2A, 2B and 26 depending upon the lead detected.

The probe 490 also includes a user interface (U/I) 495 which may be a touch sensitive screen, keypad, buttons, knobs and the like. The U/I 495 is configured to accept inputs from the user to control modes and operation of the probe 490.

FIG. 5 illustrates a comparator circuit 500 utilized within the SPC 312 in accordance with an embodiment. In FIG. 5, the comparator circuit 500 may be implemented as an operational amplifier 502. In the example of FIG. 5, the amplifier 502 is an amplifier AD624 provided by Analog Devices and having sixteen input terminals. Input terminals 1-2 represent the inputs for receiving the measured signal along lines 314, 315 (FIG. 3) from the surface electrodes 304-305. Input terminals 3, 11, 13 and 16 may be interconnected with one another in various manners to define an amount of a gain to be exhibited by the amplifier 502. Input terminals 4-8 are coupled to ground and positive and negative DC power supplies to provide the operational range for the amplifier 502. Terminal 9 represents an output terminal that produces a difference signal representing the difference between the measured signals received at terminals 1 and 2, and as determined by the gain defined by the interconnection of terminals 3, 11-13 and 16. By way of example only, when input terminals 16 and 12 are connected together, and input terminals 11 and 13 and 3 are connected together, this combination sets the gain of the amplifier at 1000. By adjusting the interconnection of terminals 3, 11-13 and 16, the gain of the amplifier may be programmed to different levels such as between 1, 100, 200, 500 and 1000. The gain may be switched under user control such as through the user interface 332 or 495. Optionally, the gain may be switched automatically by the controller 336 and/or SPC 312, such as periodically, randomly or based on a level of the companies signal. The amplifier 502 provides low noise (e.g., 0.2 microvolts peak to peak between 0.1 Hz to 10 Hz). The amplifier 502 also affords low non-linearity, high CMRR, low input offset voltage, and low input offset voltage drift.

In accordance with at least one embodiment, the comparator 500 within the probe 302 is able to capture relatively small current signals, such as when one milliamp is delivered from an implanted electrode that is positioned between 8 and 10 inches away from the skin surface and thus away from the surface electrodes. The lead information may include a graph illustrating a capacitive curvature of the signal that is detected at the probe and presented on the display.

The probe 302 affords a tool for design research and patient diagnosis of mechanical movement for electrical issues experienced by implanted NS devices and NS leads. When a known electrode pattern is present, the lead information may utilize inverting and non-inverting inputs to the comparator 500 to determine the polarity of a field and display of positive or negative pulse.

It should be recognized that alternative circuit designs and components may be utilized in place of the comparator 500. Optionally, multiple comparators 500 may be used when multiple electrode pairs are provided in the probe 302. Certain comparators 500 may be configured to search for different types of signal or depth electrodes.

Figure 6:
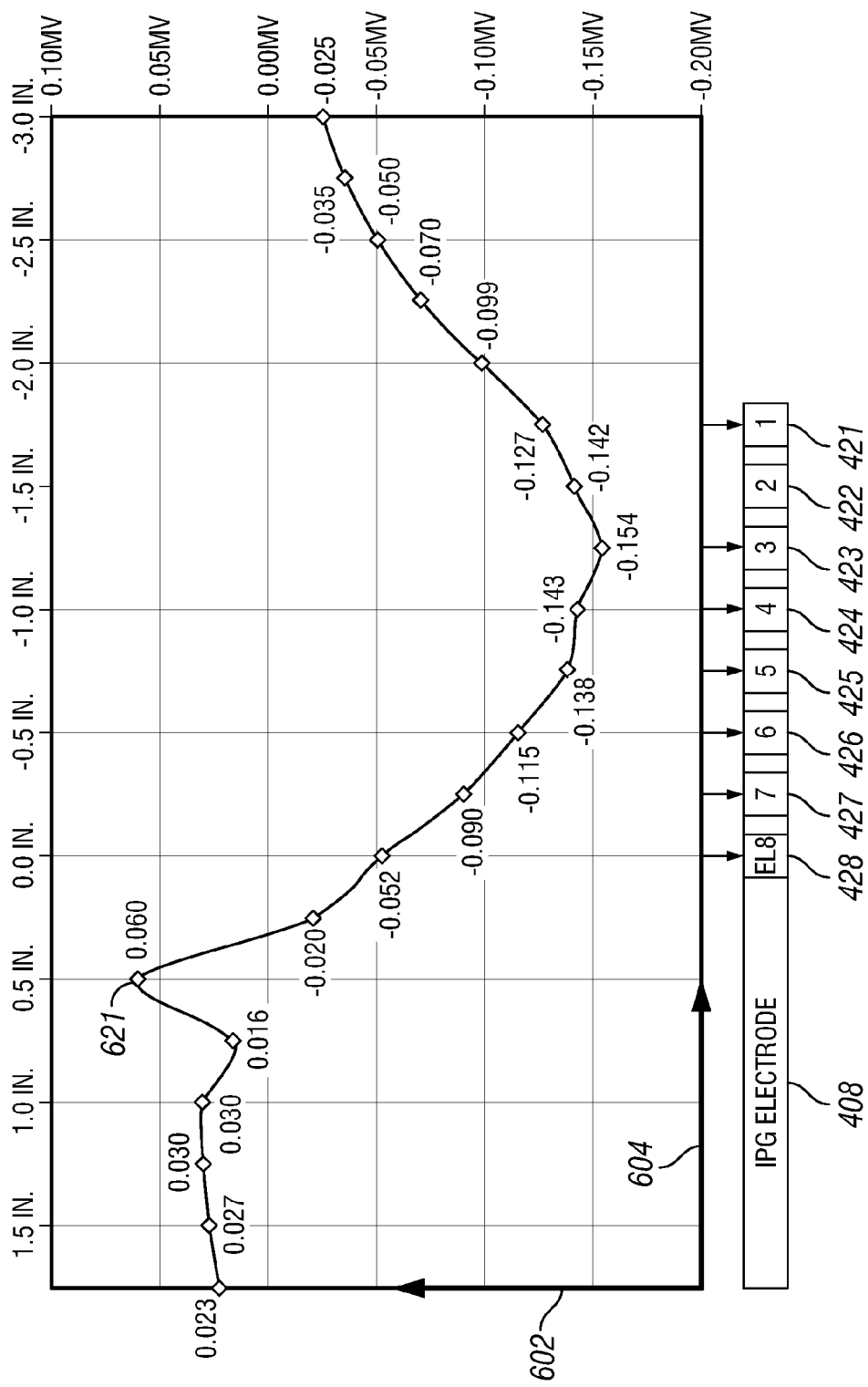
FIG. 6 illustrates an example of a difference signal that may be output by the comparator in accordance with an embodiment.

FIG. 6 illustrates an example of a difference signal that may be output by the comparator 500 of FIG. 5 as the probe 302 is moved along the skin surface 14 relative the NS lead 408. FIG. 6 illustrates one exemplary type of lead information that may be displayed to a user on the display 334 (FIG. 3). The graph 600 represents a two-dimensional field strength graph. The graph 600 plots voltage in millivolts along the vertical axis 602 and distance in the probe scan direction along the horizontal axis 604. The distances 604 are denoted in half inch increments, while the voltages along the vertical axis 602 are denoted in 0.5 mV increments. The distances along the horizontal axis 604 are measured along a probe scan direction 430 that extends generally parallel to the longitudinal axis 409 of the lead 408. The data points within the graph 600 generally correspond to the difference in the field strength at the central axis 454 that extends perpendicular to the patient engaging surface 350 of the probe 302. The central axis 454 is substantially centered between the electrodes 304 and 305.

The central axis 454 represents the center point of sensitivity for the comparator 500 between the electrodes 304 and 305. As the probe 302 is moved along the skin surface 410, the difference signal between the measurements at electrodes 304 and 305 fluctuates as shown. By way of example, when the central axis 454 of the probe 302 is 0.5 in away from the eighth electrode 428 on the lead 408, a difference signal of 0.060 mV is measured (see data point 621). As the probe 302 is moved closer to the electrodes 421-428, the difference between the signals sensed at electrodes 304 and 305 reduces. For example, when the central axis 454 of the probe 302 is aligned with electrode 428, the difference signal equals a negative 0.052 mV. When the central axis 454 of the probe 302 is centered over electrode 424, the difference signal is measured to be a negative 0.143 mV.

It should be recognized that the measurements and distances illustrated in FIG. 6 are simply exemplary and will vary depending upon the architecture of the probe, position of the lead, type of lead, pulse configuration, pulse amplitudes and the like.

In the example of FIG. 6, as is illustrated, the comparator 500 will find a strongest point in the electrical field strength produced by the lead 408 when the surface electrodes 304, 305 are positioned over the center region of the set of implanted electrodes 421-428 that are outputting stimulation pulses. The example of FIG. 6 may represent an exemplary implementation in which an SCS electrode is implemented and the highest field amplitudes are recorded between designated vertebrae.

Figure 7:
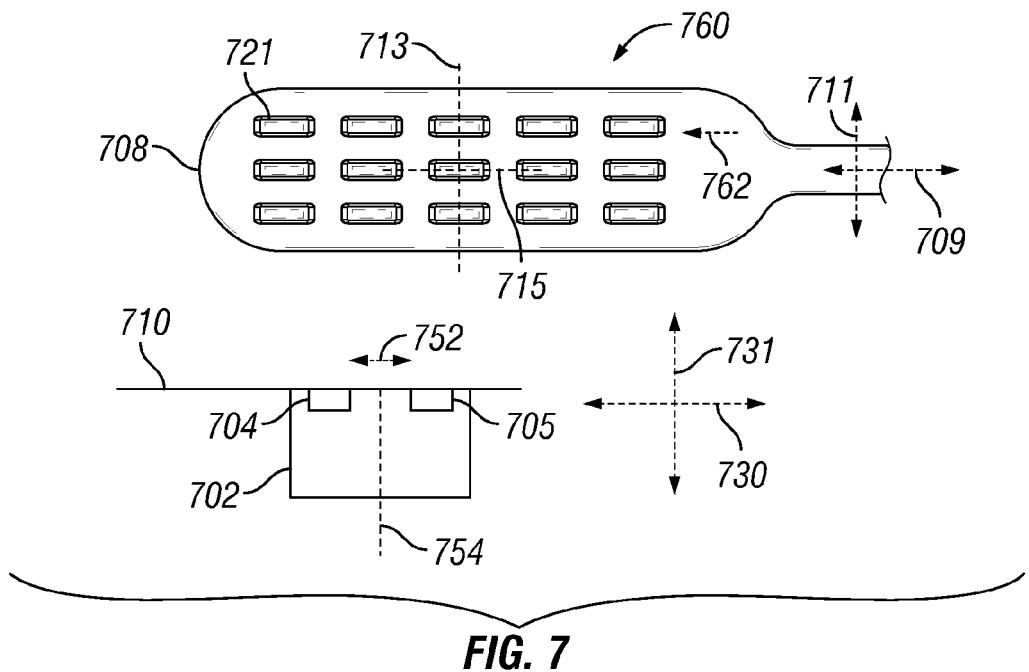
FIG. 7 illustrates an alternative embodiment in which a probe is utilized to sense a patch type lead in accordance with an embodiment.

FIG. 7 illustrates an alternative embodiment in which a probe 702 is utilized to sense a patch lead 708. The patch lead 708 includes a plurality of implanted electrodes 721 that are arranged in a two-dimensional array of rows 760 and columns 762 across the front face of the lead body. A distal portion of a probe 702 is positioned against or proximate to the surface of the patient's skin 710. The probe 702 includes two or more surface electrodes 704-705 that are separated by an interelectrode gap 752 and arranged on opposite sides of a center axis 754. The probe 702 is moved in two dimensions as denoted by longitudinal and lateral scan directions 730 and 731 along the surface 710 to collect measured signals representative of the stimulus output from the patch lead 708.

The probe 702 may be moved in the longitudinal scan direction 730 which is generally parallel to the longitudinal axis 709 of the patch lead 708 to collect one type of lead information, such as longitudinal position. The probe 702 may be moved in the lateral scan direction 731 which is generally parallel to the transverse axis 711 of the patch lead 708 to collect another type of lead information, such as lateral position. As the probe 702 is moved back and forth in the direction of 730, lead information is collected, such as to identify the longitudinal center of the lead 708 as denoted by dashed line 713. The probe 702 may be moved back and forth along the lateral scan direction 731 until identifying lead information that denotes the lateral center of the lead 708 as denoted by dashed line 715.

Figure 8:
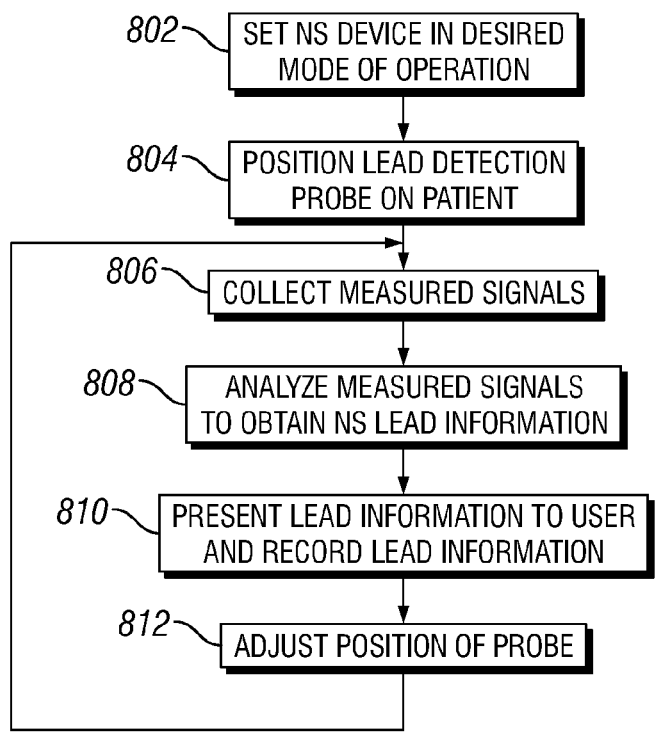
FIG. 8 illustrates a process implemented in accordance with an embodiment to detect and analyze implanted NS leads and NS devices in accordance with an embodiment.

FIG. 8 illustrates a process implemented in accordance with an embodiment to detect and analyze implanted leads and NS devices. Beginning at 802, the NS device is set into a desired mode of operation. For example, the NS device may be set to deliver a predetermined pulse or pulse sequence once or repeatedly from a single electrode, from a subset of the electrodes, all electrodes or otherwise. Once the NS device begins producing a stimulus output in accordance with the settings at 802, the lead detection probe is positioned against the patient skin in a region believed to be generally proximate to the implanted lead.

At 806, measurement signals are collected from the electrodes within the probe. At 808, the measured signals are analyzed to obtain implanted lead information. At 810, the lead information is presented to the user in a desired format and is recorded in the memory of the detector. For example, the lead information may be presented as a graph or numeric data. Alternatively, the lead information may be presented as analytical data, such as indicating pulse width, frequencies, amplitudes, pulse sequences, modes of operations and the like. At 812, the position of the probe is adjusted. The operations at 806-812 are continuously repeated in a real-time manner such that the user is able to move the probe continuously over the surface of the patient and obtain substantially contemporaneous real-time information about the lead and the NS device.

The presenting operation may include displaying to the user a graphical representation of the measured stimulation output including a pulse sequence having at least one pulse void therein corresponding to a location in the pulse sequence associated with a failed electrode. The presenting operation may include displaying to the user a graphical representation of a measured pulse sequence that includes a blank area in the pulse sequence where a pulse should have been measured, but did not occur due to a faulty electrode. The presenting operation may include co-displaying measured and programmed stimulation outputs for comparison by the user to determine where a fault exists.

The process of FIG. 8 utilizes one or more instrumentation amplifiers with pairs of closely spaced electrode inputs (electrode # 1 and 2) and a third fixed electrode (electrode #3 attached to the foot or arm) for grounding purposes. The two closely spaced electrodes # 1 and 2 are a fixed distance from each other and moved along the skin of the human body to locate and display stimulation. This affords a tool for externally locating electrodes, diagnosing and displaying the actual real time output of electrical implantable devices implanted within the patient. This can be done by contacting the skin of the patient with the amplifier's electrodes then moving the amplifier electrodes 1 and 2 closer to the strongest point of stimulation by observing the amplifiers output amplitude increase as the amplifier electrodes move closer to the strongest point of stimulation. The electrical detector or amplifier can locate and display the current capacitive and resistive characteristics of stimulation with a high level of resolution and accuracy portrayed on a display. The device may detect and/or display a 1 mA signal at a distance of 8.75 inches from the source. The higher the stimulator outputs, the better the resolution becomes at large distances. Typically, at 4 mA and up, the device exhibited high resolution from 8.75". The larger the electrode pattern, the higher the resolution for smaller amplitude outputs. The closer the amplifier electrodes move towards the source the higher the amplifier's output amplitude (amplified stimulation). This gives an indication of distance versus amplifier output amplitude. The pulse width and frequency remain a constant per the programmed parameters of the NS device. This amplifier utilizes variable gain adjustments so the entire amplitude of the signal can be displayed when the source stimulation amplitude reaches higher levels. The accuracy of the programmed parameters pulse width, frequency, and discharge mode, outputted from the amplifier is well within our product specifications.

Figure 9:
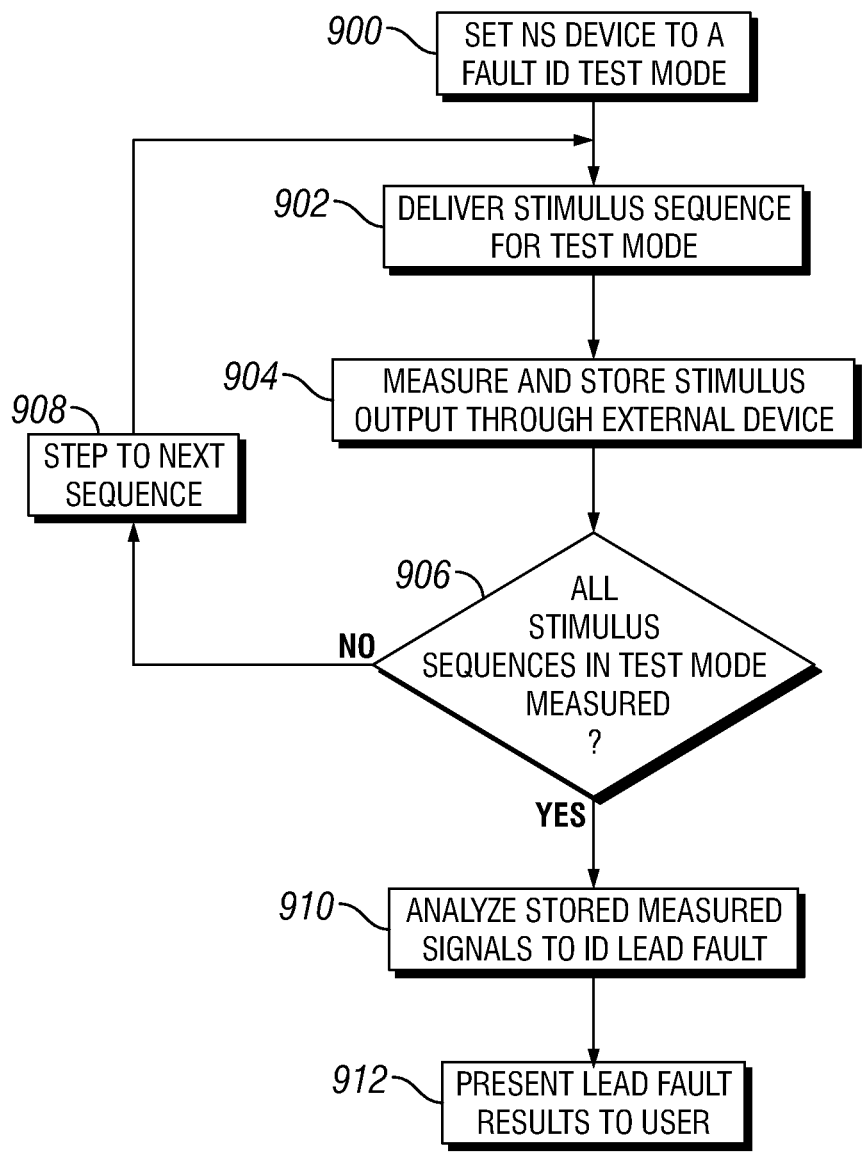
FIG. 9 illustrates a process carried in connection with identifying faults in leads in accordance with an embodiment.

FIG. 9 illustrates a process carried in connection with identifying faults in leads, such as electrodes that operate intermittently or fail. Beginning at 900, the process sets the NS device to a fault identification test mode. The fault identification test mode may be prerecorded in the NS device. Optionally, the fault identification test mode may be transmitted to the NS device from an external programmer or from the external test device described above in connection with FIGS. 3-8.

Once the NS device is set to the test mode, at 902 the NS device begins delivering one or more stimulation output sequences associated with the test mode. For example, a single test mode may include delivering a sequence of stimulation outputs from an individual electrode on the NS lead. Alternatively, the sequence may involve delivering stimulation outputs from set combinations of electrodes on the NS lead. The combinations of electrodes, by way of example only, may include delivering pulses from set combinations of electrodes simultaneously. Alternatively, the sequence may include delivering pulses from different electrodes in a predetermined sequence with predetermined delays therebetween. At 902, a stimulation sequence from the test mode is repeating delivered.

At 904, the external test device measures stimulation outputs through the external probe (e.g., 302). At 904, measurement signals are collected by the external probe and stored in connection with the current stimulation sequence being delivered by the NS device. Once a sufficient number of measured signals are collected and stored in connection with the stimulation outputs produced by the current stimulation sequence, flow moves to 906 where it is determined whether additional stimulation sequence exists within the current test mode. An individual test mode may include a series of stimulation sequences. For example, for a lead having eight electrodes arranged along the length of the lead, a test mode may include a separate stimulation sequence associated with each of the eight electrodes. Hence, during a first iteration through the operations at 902 and 904, a first stimulation sequence may deliver a series of pulses only from the first electrode.

At 906, it would then be determined whether additional stimulation sequences need to be delivered from the other seven electrodes upon the lead. The operations at 902-906 are iteratively performed, such that a separate stimulation sequence would be implemented for each of the eight electrodes in the present exemplary lead. At 906, when it is determined that additional stimulation sequences are to be tested, flow moves to 908 where the process steps to the next sequence. Flow then returns to 902 and the NS device delivers the next stimulation sequence from the test mode. At 906, after all of the stimulation sequences for the current test mode have been delivered and measured signals collected and stored in connection therewith, flow moves to 910. At 910, the measured signals associated with each of the stimulation sequences are then analyzed. Various types of analysis may be performed at 910. For example, the measured signals from each of the stimulation sequences may be analyzed separately to determine whether each electrode upon a lead delivered the desired number of pulses with the desired pulse amplitude, pulse width, pulse timing and the like. Alternatively, the measured signals from the stimulation sequences may be analyzed in pulse shape, temporal delivery, correlation and the like.

At 912, the results from the analysis at 910 are presented to the user. For example, at 912, the lead fault results may be presented to the user by informing the user that an individual electrode or electrode on a lead have remained open and did not deliver expected stimulation outputs. Alternatively, the lead fault results may inform the user that one or more of the electrodes operated intermittently, namely delivering some expected stimulation output pulses but not all intended stimulation output pulses. As a further result, the lead fault result may inform the user that pulse amplitudes or pulse shapes were not proper when delivered by one or more electrodes. The lead fault results may identify specific electrodes on a lead that exhibit particular faults, or simply indicate that one or more of the electrodes exhibit a fault without identifying the specific electrode exhibiting the fault. As a further option, the lead fault results may includes likelihoods of probabilities that a particular fault has occurred. For example, when identifying a particular fault, the results may inform the user that there is a high likelihood that electrode number one is exhibiting an intermittent behavior or is open. As another example, the lead fault results may inform the user that there is a medium likelihood that one of electrodes three through six are open. Other types of results may be presented to the user depending upon a particular type of electrode, a particular type of lead, the position of the lead and the like.

Figure 10A:
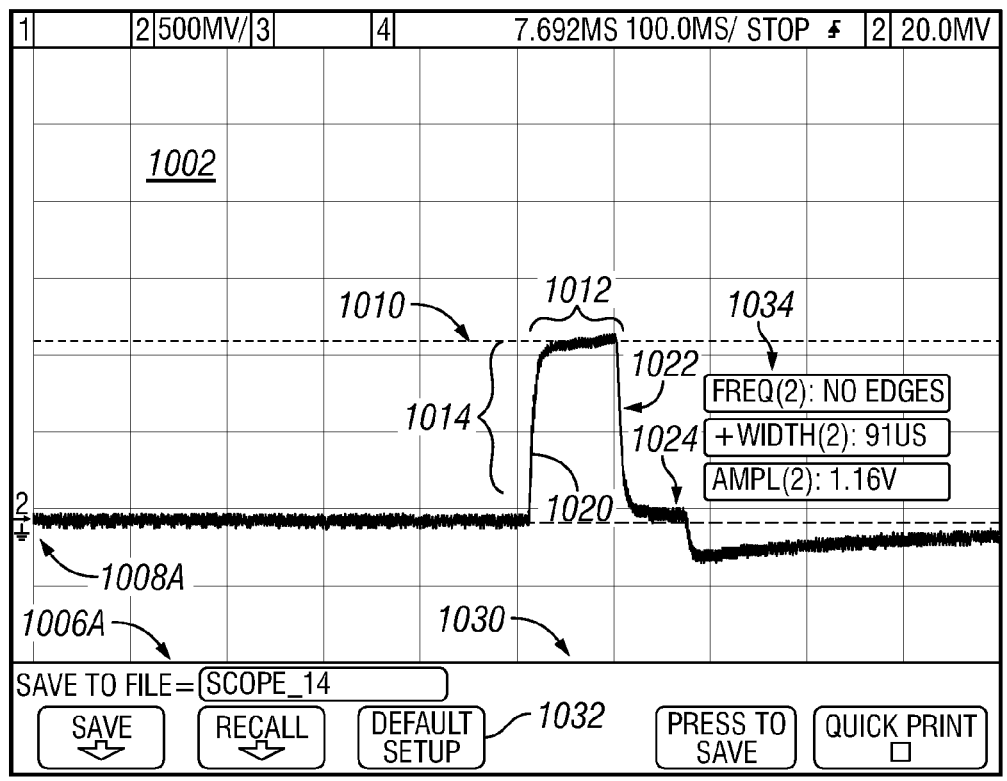
FIG. 10A-10C illustrates a pulse output by the lead and sensed by the surface electrodes.
Figure 10B:
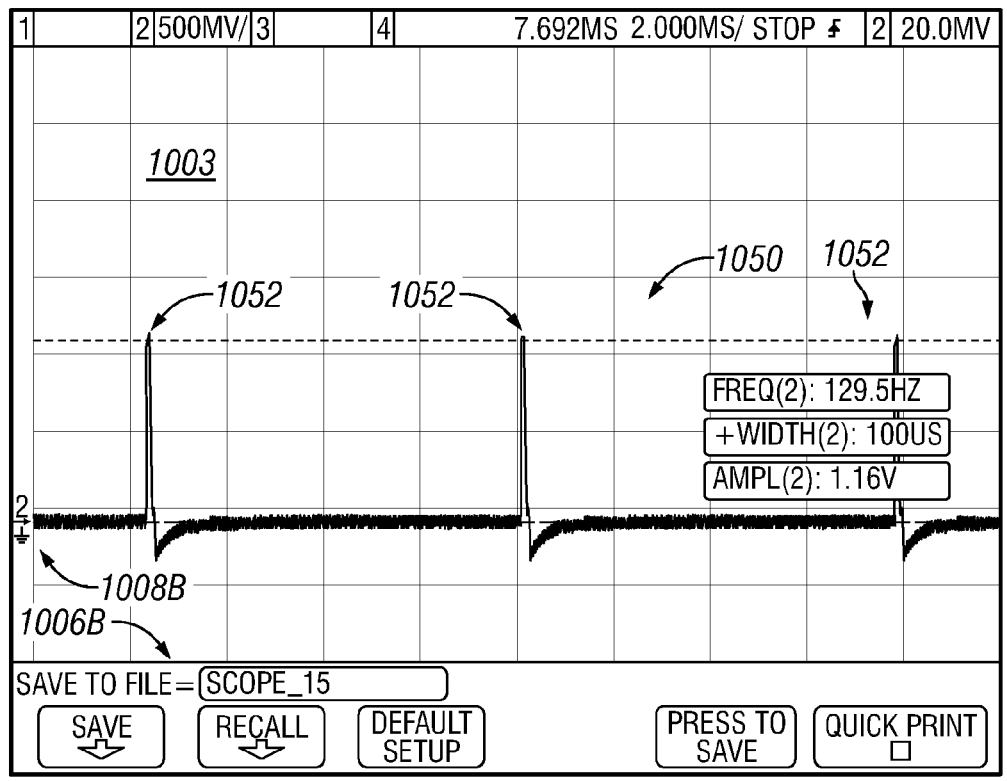
Figure 10C:
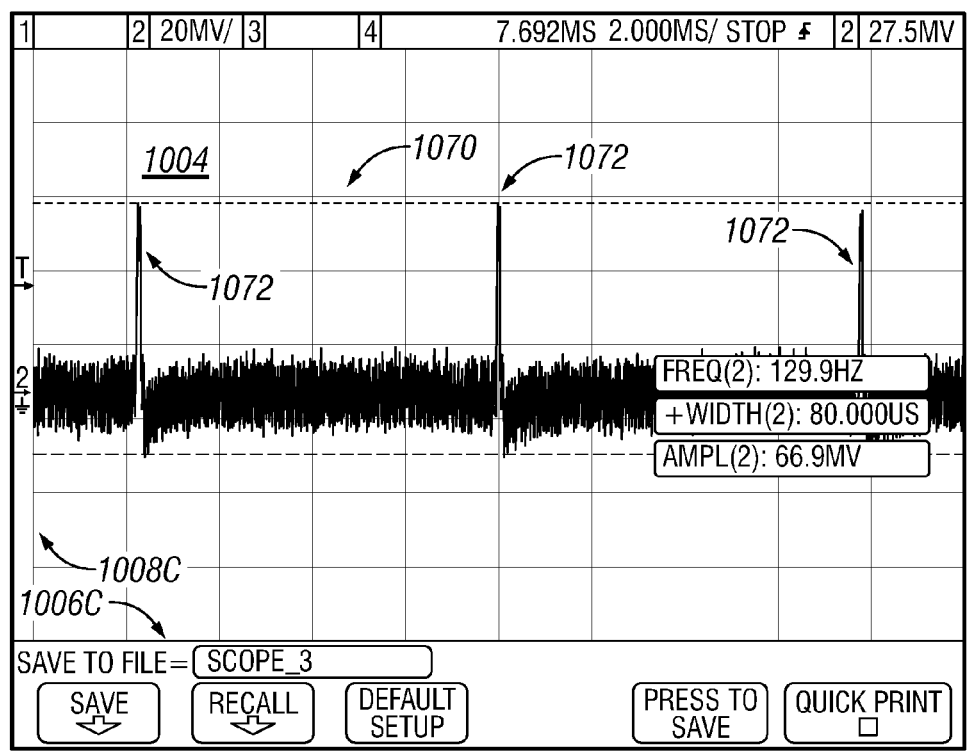

FIGS. 10A-10C illustrate examples of how lead information may be presented on the display 334 or 492. FIGS. 10A-10C illustrate graphs 1002-1004 of comparator signals resulting from the comparison of two or more measured signals. The graphs 1002-1004 indicate time along the horizontal axis 1006A-C and voltage along the vertical axis 1008A-C. In FIG. 10A, the vertical axis 1008A is separated into 500 mV increments, while the horizontal axis 1006A is separated into 100 uSec increments.

FIG. 10A illustrates a pulse 1010 output by the lead and sensed by the surface electrodes. The pulse 1010 has a width 1012 of approximately 91 uSec, amplitude 1014 of approximately 1.16V. The pulse 1010 includes a leading edge 1020, trailing edge 1022, tail 1024 and other parametric properties that may be of interest and may be measured. The parametric properties of the pulse may be measured manually from the display by a user or may be automatically measured by the detector. The pulse 1010 is delivered from one electrode, a subset of electrodes or collectively from all of the electrodes on the lead. By analyzing the amplitude, pulse width, pulse shape, pulse leading edge, pulse trailing edge, tail and the like, a user may determine whether the active electrode(s) are delivering a stimulation output with the desired parametric properties. The display may also present additional lead & device related information 1030 such as the setup or mode 1032 in which the device is presently operating and the like. When a single electrode or a subset of electrodes are being used to deliver pulse 1010, the lead and device related information 1030 may identify which individual electrode or electrodes are currently generating a stimulation output. For example, the detector may analyze the parametric properties of interest from the pulse and may output the analysis as lead information on the display such as in analytic data area 1034.

FIG. 10B illustrates a graph 1003 in which the vertical axis 1008B has the same time scale as in FIG. 10A, but the horizontal axis 1006B has been adjusted to a different time scale spanning a longer period of time than in FIG. 10A. The vertical axis 1008B is separated into 500 mV increments, while the horizontal axis 1006B is separated into 2 mSec time increments. FIG. 10B illustrates a pulse sequence 1050 output by the lead and sensed by the surface electrodes. The pulse sequence 1050 includes a series of pulses 1052 successively output by the same electrode or electrodes. The pulses 1052 have a width of approximately 100 uSec, amplitude of approximately 1.16V and a frequency of 129.5 Hz. Each of the pulses 1052 includes a leading edge, trailing edge, tail and other parametric properties that may be of interest and may be measured. The parametric properties may also include frequency, duty cycle and the like. The pulse sequence 1050 is delivered from one electrode, a subset of electrodes or collectively from all of the electrodes on the lead. By analyzing the frequency, duty cycle, amplitude, pulse width, pulse shape, pulse leading edge, pulse trailing edge, tail and the like, a user may determine whether the active electrode(s) are delivering a stimulation output with the desired parametric properties. When a single electrode or a subset of electrodes are being used to deliver pulse sequence 1050, the lead and device related information may identify which individual electrode or electrodes are currently generating a stimulation output.

The detector measures the parametric properties of interest from the pulse sequence and may output this lead information on the display such as in analytic data area 1054.

FIG. 10C illustrates a graph 1004 in which the vertical axis 1008C and horizontal axis 1006C have different time scales than FIG. 10A. The vertical axis 1008C is separated into 20 mV increments, while the horizontal axis 1006C is separated into 2.000 mSec time increments. FIG. 10C illustrates a pulse sequence 1070 output by the lead and sensed by the surface electrodes. The pulse sequence 1070 includes a series of pulses 1072 successively output by the same electrode or electrodes. The pulses 1052 have a width of approximately 80.00 uSec, amplitude of approximately 66.9 mV and a frequency of 129.5 Hz.

Figure 11:
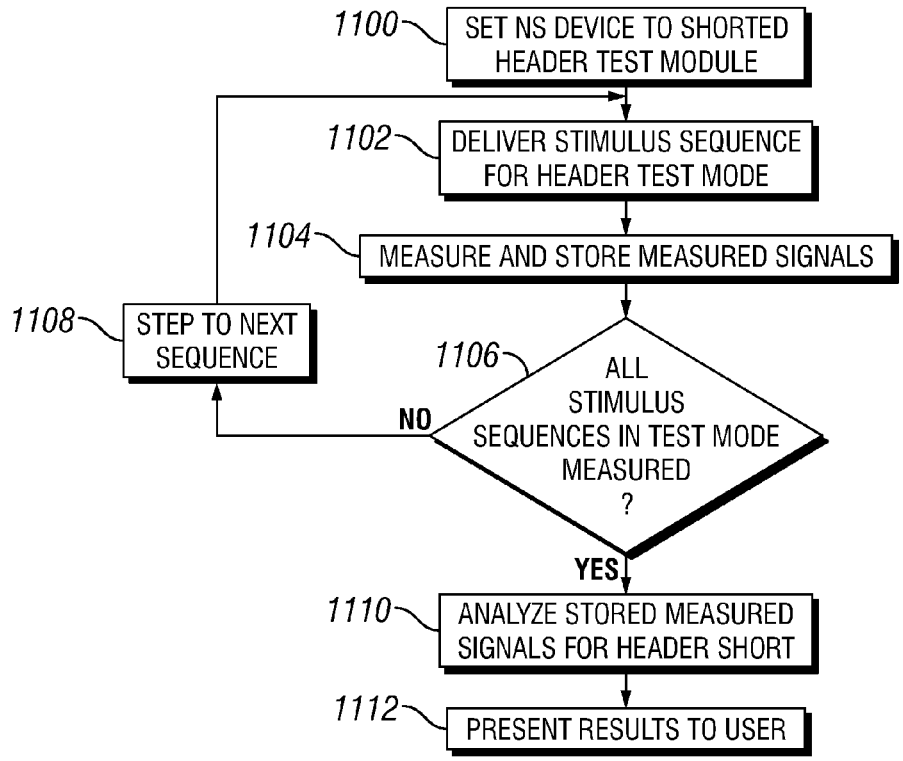
FIG. 11 illustrates a process carried in connection with identifying short circuits in an NS device header.

FIG. 11 illustrates a process carried in connection with identifying short circuits in an NS device header. When a short circuit occurs in the header, this may lead to electrodes failing to operate at all, operating intermittently or delivering pulses having an improper pulse shape (e.g., low pulse amplitude, faulty pulse leading edge, faulty pulse trailing edge and the like). Beginning at 1100, the process sets the NS device to a header short circuit identification test mode. The header short circuit identification test mode may be prerecorded in the NS device. Optionally, the header short circuit identification test mode may be transmitted to the NS device from an external programmer or from the external test device described above in connection with FIGS. 3-8.

Once the NS device is set to the test mode, at 1102 the NS device begins delivering one or more stimulation output sequences associated with the test mode. For example, a single test mode may include delivering a set or sequence of stimulation outputs from an individual electrode on the NS lead. Alternatively, the set or sequence may involve delivering stimulation outputs from set combinations of electrodes on the NS lead. The combinations of electrodes, by way of example only, may include delivering pulses from set combinations of electrodes simultaneously. Alternatively, the set or sequence may include delivering pulses from different electrodes in a predetermined sequence with predetermined delays there between. At 1102, a stimulation set or sequence from the test mode is repeating delivered.

At 1104, the external test device measures stimulation outputs through the external probe (e.g., 302). At 1104, measurement signals are collected by the external probe and stored in connection with the current stimulation sequence being delivered by the NS device. Once a sufficient number of measured signals are collected and stored in connection with the stimulation outputs produced by the current stimulation sequence, flow moves to 1106 where it is determined whether additional stimulation set or sequence exists within the current test mode. An individual test mode may include a series of stimulation sequences. For example, for a lead having eight electrodes arranged along the length of the lead, a test mode may include a separate stimulation sequence associated with each of the eight electrodes. Hence, during a first iteration through the operations at 1102 and 1104, a first stimulation sequence may deliver a series of pulses only from a first electrode on the lead. During a second iteration through the operations at 1102 and 1104, a second stimulation sequence may deliver a series of pulses only from a second electrode on the lead, and so forth.

At 1106, it is determined whether additional stimulation sequences need to be delivered from the other electrodes upon the lead. The operations at 1102-1106 are iteratively performed, such that a separate stimulation sequence would be implemented for each of the eight electrodes in the present exemplary lead. At 1106, when it is determined that additional stimulation sequences are to be tested, flow moves to 1108 where the process steps to the next sequence. Flow then returns to 1102 and the NS device delivers the next stimulation sequence from the test mode. At 1106, after all of the stimulation sequences for the current test mode have been delivered and measured signals collected and stored in connection therewith, flow moves to 1110.

At 1110, the measured signals associated with each of the stimulation sequences are then analyzed. Various types of analysis may be performed at 1110. For example, the measured signals from each of the stimulation sequences may be analyzed separately to determine whether each electrode upon a lead delivered the desired number of pulses with the desired pulse amplitude, pulse width, pulse timing and the like. Alternatively, the measured signals from the stimulation sequences may be analyzed for pulse shape, temporal delivery, correlation and the like.

At 1112, the results from the analysis at 1110 are presented to the user. For example, at 1112, the header short circuit results may be presented to the user by informing the user that a header short circuit has occurred. Alternatively, the header short circuit results may inform the user that one or more of the header is operating intermittently, namely delivering some expected stimulation output pulses but not all intended stimulation output pulses. As a further result, the header short circuit result may inform the user that pulse amplitudes or pulse shapes were not proper when delivered by one or more electrodes. The header short circuit results may identify specific aspects of the header that exhibit particular faults, or simply indicate that the header exhibits a fault without identifying the specific fault within the header. As a further option, the header short circuit results may includes likelihoods of probabilities that a particular fault has occurred. Other types of results may be presented to the user depending upon a particular type of NS device, a particular type of header or lead and the like.

Figure 12:
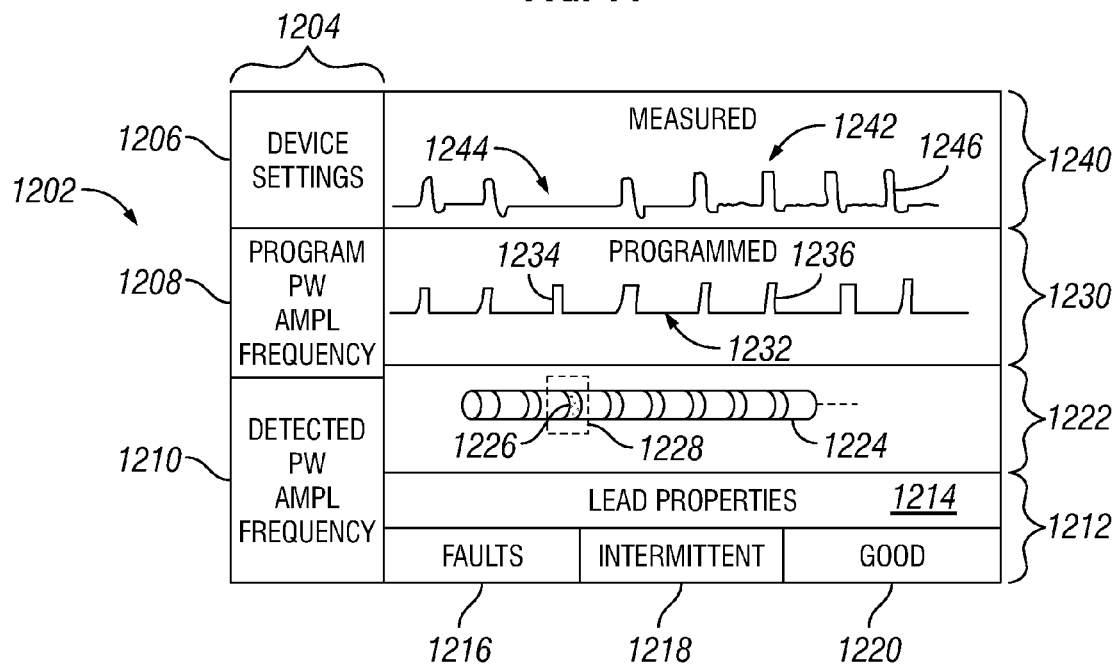
FIG. 12 illustrates exemplary windows with the types of information that may be presented to the user on the display.

FIG. 12 illustrates an example of the type of information that may be presented to the user on the display. In FIG. 12, a display 1202 is illustrated with a group of windows presenting different types of information. The display 1202 includes a device setting window 1204 in which the present settings are displayed for the NS device, in order to inform the user regarding how the NS device should operate. The device setting window 1204 includes an area 1206 for general device settings and an area 1208 that indicated the programmed stimulation settings for parametric properties of interest, such as the pulse width, amplitude, frequency and the like. The programmed settings may correspond to the current set or sequence of stimulation outputs, for a single stimulation output and the like. A detected output area 1210 is included near the programmed stimulation setting area 1208. The detected output area 1210 may include a listing of values that were measured by the probe 302 for the parametric properties of interest, such as the pulse width, amplitude, frequency and the like.

The display 1202 also includes a lead properties window 1212 in which the properties of an implanted lead are displayed for the NS lead, in order to inform the user regarding what type of lead is implanted. The lead properties setting window 1212 includes an area 1214 for general lead properties (e.g., 9 electrode paddle lead, 12 electrode paddle lead, 8 electrode Lamitrode lead, etc) and measured electrode status areas 1216, 1218 and 1220 that indicated the information about individual electrodes, such as which electrodes have failed (area 1216), which electrodes are operating intermittently (area 1218) and which electrodes are good (1220).

The display 1202 also includes a lead graphical area 1222 that may present a 2D or 3D image of the type of lead that is implanted, as illustrated by lead image 1224. The lead image 1224 may include indicia to identify failed and/or faulty electrode(s) such as failed electrode 1226. Optionally, a faulty or intermittent electrode may be designated in the lead image 1224 by indicia 1228 which may represent a boundary line, border, colored area, flashing portion of the lead image 1224 and the like.

The display 1202 also includes a programmed stimulation window 1230 that illustrates a representation of the programmed stimulation output 1232 that the NS device is intended to generate. The programmed stimulation output 1232 may include one or more pulses 1234, 1236 with the programmed pulse width, amplitude, and frequency listed in area 1208. The content of the window 1230 may be varied to inform the user of what stimulation output(s) the NS device should produce based on the present mode of operation and programmed settings.

The display 1202 also includes a measured stimulation window 1240 that illustrates a graphical representation of the measured stimulation output 1242 that was measured by the surface electrodes and analyzed by the SPC 312 and controller 336. For example, the measured stimulation output 1242 may correspond to the comparator signal output by the amplifier 500. The measured stimulation output 1242 includes one or more pulses 1246 with the measured pulse width, amplitude, and frequency listed in area 1210. In the example of FIG. 12, the implanted lead includes one faulty electrode (corresponding to electrode 1226). Thus, the measured stimulation output 1242 has a pulse void 1244 in the pulse sequence. The pulse void is represented by a blank area in the pulse sequence where a pulse should have been measured, but did not occur due to the faulty electrode 1226. The measured and programmed stimulation outputs 1242 and 1232 may be co-displayed side by side, above one another or in an overlapped manner. By comparing the measured and programmed stimulation outputs 1242 and 1232, the user may readily determine where the fault is located.

Optionally, one or more of the windows discussed above may be omitted. Optionally, the content of the window 1240 may be varied to inform the user of what stimulation output(s) the NS device should produce based on the present mode of operation and programmed settings.

Embodiments described herein provide a tool useful after implantation to monitor various parametric properties of the NS system. For example, embodiments permit analysis of the operation of the NS device, such as the discharge mode, pulse sequency, pulse width and frequency for the stimulation output of the NS device. Further, embodiments herein permit the NS lead to be located and more specifically, to locate the position and/or identity inoperative and operative electrodes on the NS lead. After implementation, the potential exists for NS leads to move or migrate within the patient. Embodiments herein afford a reliable and practical mechanism to readily identify lead migration. Embodiments herein afford a reliable and practical method for a physician or representative to locate the lead's position in connection with reprogramming or physical intervention. Once the new position of the lead is identified, the physician then reprograms the lead, such as to use a different set of electrodes on the lead to deliver the stimulus output. Embodiments described herein avoid exposing the patient to radiation each time a fluoroscopy is performed, which is not desirable.

Embodiments described herein provide reliable and practical ways to identify lead malfunctions. Lead malfunctions may occur due to physical failure or breaks within the lead conduction and/or electrical failures within the NS device. When a physical failure or break causes a lead to operate intermittently or not at all, embodiments described herein are able to diagnose the intermittent and open leads down to the electrode.

Embodiments described herein provide a tool that enables data logging for research to enable patient anomalies to be recorded in connection with stimulation outputs while an NS lead is in the patient. Embodiments described herein provide a tool that informs an EMT that the person has an implantable device, and informs the EMT of the location of the implantable device. Embodiments described herein provide a tool that affords a quick method of determining what type of device the patient has within them, and the location of the device.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. An external system to detect an implanted lead coupled to an implanted neurostimulation device (INSD), the system comprising:
    a handheld probe having electrodes configured to be positioned external to a surface of a patient and proximate to a region of the patient having the implanted lead for an INSD, the electrodes configured to measure a stimulation output from the implanted lead of the INSD;
    a controller coupled to the electrodes to receive measured signals from the electrodes, the measured signals representative of the stimulation output of the INSD, the controller processing the measured signals to obtain lead information;
    an amplifier that compares the measured signals to obtain a difference signal, the difference signal increasing as the electrodes move closer to a source of the stimulation output; and
    a user interface to present the lead information to a user, the lead information indicative of at least one of an operation of the lead and a position of the lead.

2. The system of claim 1, wherein the lead information includes at least one of discharge mode, pulse width and frequency for the stimulation output of the INSD.

3. The system of claim 1, wherein the lead information includes at least one a presence, signal strength, duration and shape for the stimulation output of the INSD.

4. The system of claim 1, wherein the lead information includes at least one electrical occurrence of, and electrical anomalies in, the stimulation output of the INSD.

5. The system of claim 1, wherein the lead information includes at least one of i) information to locate the lead in the patient and ii) information to identify improper operation of the lead.

6. The system of claim 1, wherein the external electrodes include first and second electrode inputs closely spaced proximate to one another to be moved along skin of the patient while locating the lead.

* * * * *